United States Patent [19]

Igaue et al.

[11] Patent Number: 5,743,776
[45] Date of Patent: Apr. 28, 1998

[54] TOPSHEET FOR USE IN BODY FLUIDS ABSORPTIVE GOODS

[75] Inventors: Takamitsu Igaue; Hisashi Takai; Tsutomu Kido, all of Kawanoe, Japan

[73] Assignee: Uni-Charm Corporation, Ehime-ken, Japan

[21] Appl. No.: 692,404

[22] Filed: Aug. 5, 1996

Related U.S. Application Data

[63] Continuation of Ser. No. 469,738, Jun. 6, 1995, abandoned, which is a continuation of Ser. No. 191,546, Feb. 4, 1994, abandoned.

[30] Foreign Application Priority Data

Feb. 12, 1993 [JP] Japan .................... 5-024288

[51] Int. Cl.$^6$ .................... A61F 13/15; D04H 1/54; D04H 1/56
[52] U.S. Cl. .................... 442/414; 428/131; 428/212; 428/218; 604/381; 604/382; 604/385.1
[58] Field of Search .................... 428/131, 212, 428/218; 442/414; 604/381, 382, 385.1

[56] References Cited

U.S. PATENT DOCUMENTS

| | | |
|---|---|---|
| 4,741,941 | 5/1988 | Englebert et al. |
| 4,781,692 | 11/1988 | Zamarripa et al. |
| 5,154,714 | 10/1992 | Nomura . |

FOREIGN PATENT DOCUMENTS

| | | |
|---|---|---|
| 0358031 | 3/1990 | European Pat. Off. |
| 0495212 | 7/1992 | European Pat. Off. |
| 2180271 | 3/1987 | United Kingdom . |
| 2237205 | 5/1991 | United Kingdom . |
| 86/07242 A1 | 12/1986 | WIPO . |
| 91/14414 | 10/1991 | WIPO . |

*Primary Examiner*—Kathleen Choi
*Attorney, Agent, or Firm*—Lowe Hauptman Gopstein & Berner

[57] ABSTRACT

To prevent body fluids from flowing backward through a liquid-permeable topsheet for use in body fluids absorptive goods, the topsheet is formed by a nonwoven fabric made of thermoplastic synthetic fibers appropriately fused together and the topsheet is provided with openings and a skin-contacting region continuously extending around the openings. A first zone of the topsheet has a water-resistance at least in the skin-contacting region which is higher than a water-resistance in a second zone extending outside the first zone so as to suppress a back flow of body fluids possibly occurring in the skin-contacting region.

17 Claims, 2 Drawing Sheets

TOPSHEET FOR USE IN BODY FLUIDS ABSORPTIVE GOODS

This application is a continuation of application Ser. No. 08/469,738 filed Jun. 6, 1995, now abandoned, which is a continuation of application Ser. No. 08/191,546 filed Feb. 4, 1994, now abandoned.

BACKGROUND OF THE INVENTION

The present invention relates to a liquid-permeable topsheet for use in body fluids absorptive goods such as disposable diapers and sanitary napkins.

It is well known to make a liquid-permeable topsheet for use in body fluids absorptive goods from a nonwoven fabric consisting of thermoplastic synthetic fibers appropriately fused together and to provide this sheet with a plurality of openings through which body fluids can be guided toward an absorbent core, with an upper surface of the sheet being adapted to be in contact with the wearer's skin and a lower surface of the sheet being adapted to be in contact with the absorbent core.

For example, U.S. Pat. No. 4,741,941 discloses a technique to make a topsheet having liquid passages as the above-mentioned openings utilizing the process of making melt blown nonwoven fabric or spun-bonded nonwoven fabric.

Japanese patent application Disclosure Gazette No. 1992-89054 discloses a technique of making a topsheet, in which the above-mentioned openings are formed as liquid passages from a part of melt blown nonwoven fabric and these liquid passages are made air-permeable.

Both techniques as mentioned above certainly provide the topsheet made of melt blown fibers which are sufficient fine to provide the topsheet of comfortable touch. In addition, such topsheet contains a plurality of interstices contributing to improvement of air-permeability between the wearer's skin and habiliments. On the other hand, however, the presence of these fiber interstices may cause body fluids permeating through the topsheet to flow backward from the absorbent core to the wearer's skin under a pressure of the wearer's body weight.

In view of such a problem left by the prior art behind unsolved, it is a principal object of the invention to provide a topsheet for use in body fluids absorptive goods having openings functioning to guide body fluids from the upper side to an absorbent core underlying the lower side of the topsheet and a skin-contacting area continuously surrounding the openings.

SUMMARY OF THE INVENTION

The object set forth above is achieved, according to the invention, by a topsheet for use in body fluids absorptive goods having openings adapted to guide body fluids from a top surface to an absorbent core underlying a bottom surface of the sheet and a skin-contacting area continuously surrounding said opening, said topsheet being formed by a nonwoven fabric made of thermoplastic synthetic fibers appropriately fused together, wherein said topsheet has a relatively high water-resistance in said skin-contacting area defined by a first zone and a relatively low water-resistance in a second zone surrounding said first zone.

Preferably, said second zone has its water-resistance gradually decreasing as a distance from said first zone becomes longer.

Preferably, said first and second zones are having fibers interstices being filled up closer than the remaining zone.

According to the invention, the topsheet is provided with openings for passage of body fluids to make the sheet liquid-permeable. Thermoplastic synthetic fibers such as melt blown fibers may be appropriately fused together to achieve a desired soft touch. In the first zone, for example, destined to be in contact with a skin region extending around anus, the nonwoven fabric may be thermally fused together until the fiber interstices are partially filled up to improve a water-resistance and thereby body fluids may be prevented from flowing backward. In the second zone extending outside the first zone, for example, an outer peripheral region of diaper, the sheet is substantially free from a possibility of back flow without any need for filling up of the fiber interstices and this fact rather contributes to maintenance of a high air-permeability.

BRIEF DESCRIPTION OF THE DRAWINGS

The invention will be described more in detail by way of example in reference with the accompanying drawings, in which.

DESCRIPTION OF THE PREFERRED EMBODIMENTS

Figure 1:
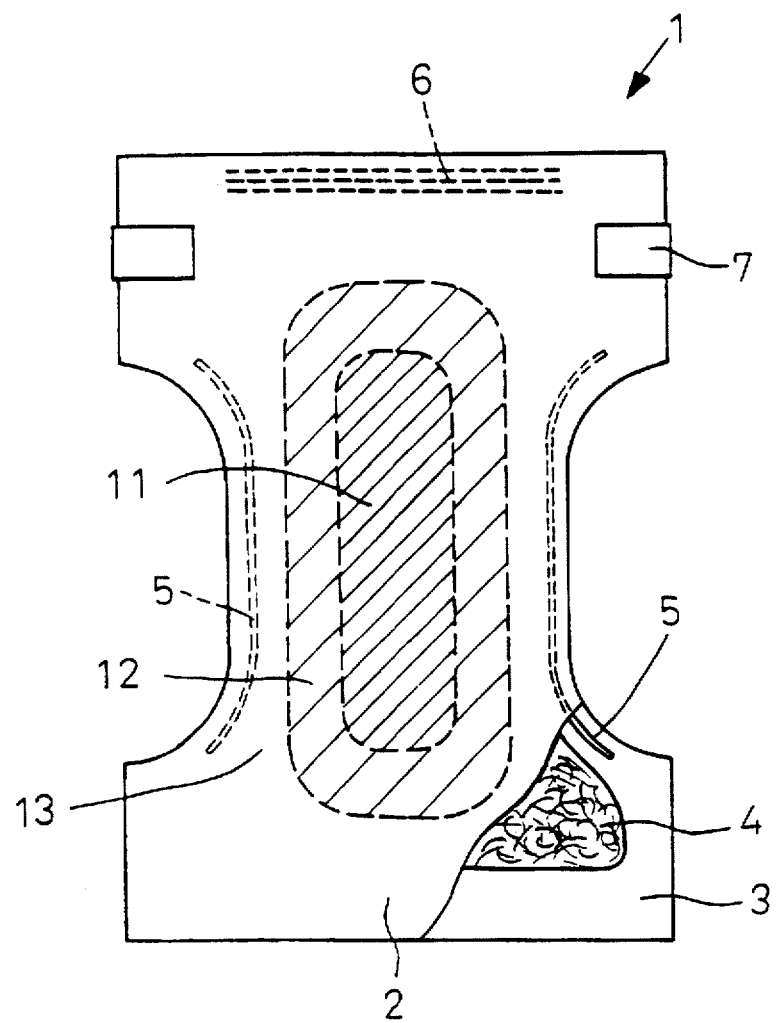
FIG. 1 is a plan view of diaper.

Referring to FIG. 1, a disposable diaper 1 is shown in a plan view as partially broken away. As shown, the diaper 1 comprises a liquid-permeable topsheet 2, a liquid-impermeable backsheet 3, an absorbent core 4 sandwiched between these sheets 2, 3, stretchable elastic members 5, 6 provided around leg-openings and along a rear waist for defining part of a waist-opening, respectively, and adhesive tape fasteners 7 fixed at respective one ends to laterally opposite side edges of the rear waist.

The topsheet 2 generally comprises a zone 11 of high water-resistance longitudinally extending in front and behind and including a crotch region of the diaper in which excretion of body fluids will be concentrated, a zone 12 of medium water-resistance surrounding said zone 11 and a zone 13 of low water-resistance surrounding said zone 12.

Figure 2:
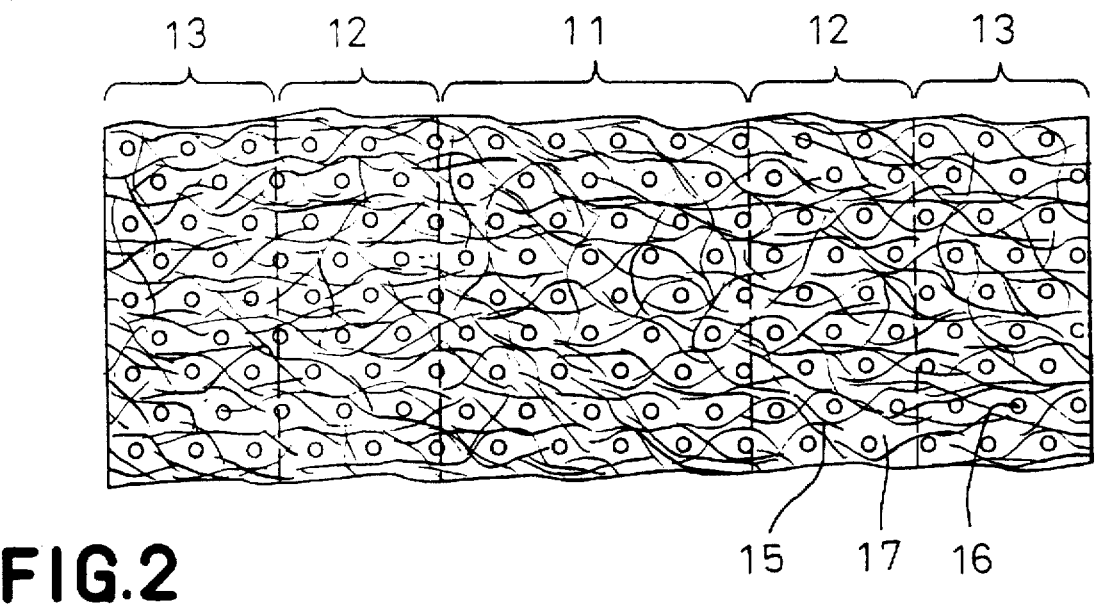
FIG. 2 is a fragmentary sectional view schematically showing, in an enlarged scale, a topsheet of the invention.

FIG. 2 is a fragmentary sectional view schematically showing the topsheet 2 in an enlarged scale. The topsheet 2 comprises a nonwoven fabric having a weight per unit area of 10 to 100 g/m² made from thermoplastic synthetic fibers appropriately fused together. As shown, the topsheet 2 has a plurality of openings 16 each extending through the sheet 2 from upper surface to lower surface of the sheet 2 and a skin-contacting area 17 continuously extending around the respective openings 16. Each opening 16 has a diameter of 0.3 to 10 mm, preferably 0.5 to 7 mm at its top and may have a diameter at its bottom either larger or smaller than the diameter at its top. In the zone 11 of high water-resistance, the nonwoven fabric may be heated under a pressure so far as a desired touch is significantly impaired to increase the degree at which individual fibers 15 are fused together until most of the fiber interstices are filled up and a water-resistance specified by JIS L-1097 reaches or exceeds 700 mm. In the zone 12 of medium water-resistance, the nonwoven fabric is treated so that the skin-contacting area 17 presents a water-resistance of 300 to 700 mm. In the zone 13 of low water-resistance, the nonwoven fabric is subjected to almost no heating under a pressure or not subjected to such a treatment at all, leaving the fiber interstices of the nonwoven fabric not filled up and thereby suppressing a water-resistance to 300 mm or lower.

The thermoplastic synthetic fibers 15 may be polyolefin fibers such as polyethylene and polypropylene fibers, or polyamide or polyester fibers. Fineness of the fibers may be 0.05 to 10 d, preferably 0.5 to 5 d. Examples of the fibers 15 and the nonwoven fabric respectively are melt blown fibers and melt blown nonwoven fabric formed by appropriately fusing such fibers together.

In the diaper 1 constructed as described, body fluids excreted on the upper surface of the topsheet 2 over the crotch area are guided through the respective openings 16 onto the absorbent core 4. When a body weight of the wearer is exerted on the absorbent core which holds the body fluids having been already absorbed therein, back flow of the body fluids may occur in the zone 11 of high water-resistance through the openings 16 but hardly occurs through the skin-contacting area 17. Zones of the diaper 1 substantially free from significant back flow of body fluids are subjected to moderate or little heat treatments so as to define the zone 12 of medium water-resistance and the zone 13 of low water-resistance, i.e., so as to keep many or most of the fiber interstices not filled up. Consequently, air-permeability and soft touch peculiar to the nonwoven fabric are hardly affected.

Figure 3:
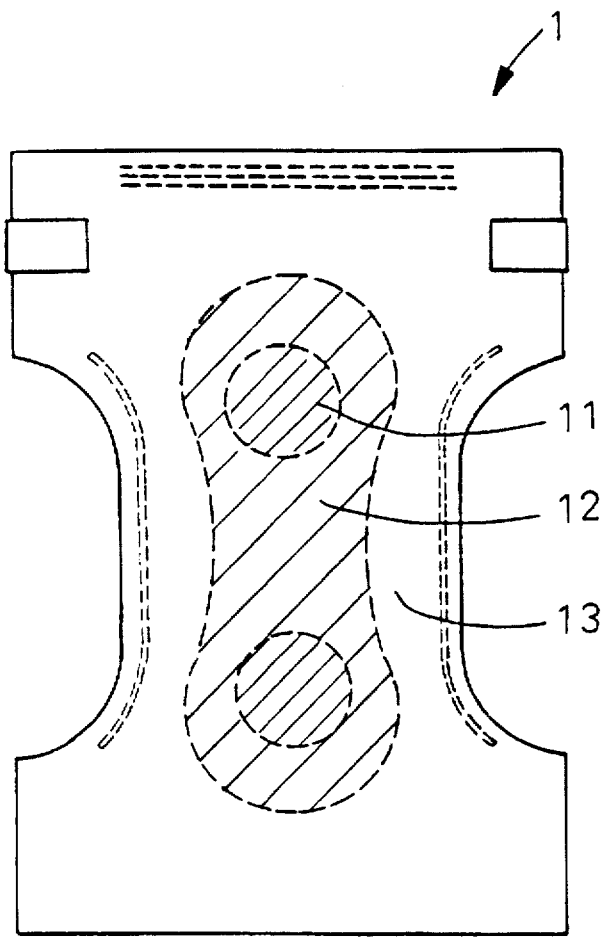
FIG. 3 is a plan view of a disposable diaper employing the topsheet of a type different from that shown in FIG. 1.

FIG. 3 is a plan view similar to FIG. 1 but showing an alternative embodiment, in which the zone 11 of high water-resistance is divided into a front body section and a rear body section. While it is preferred to distribute the zone 11 of high water-resistance on the region over which normally excretion of the body fluids is concentrated, said zone 11 may be distributed on any desired region, taking account of particular conditions for manufacturing and using the diaper 1.

To make the topsheet 2, melt blown fibers 15 may be blown against a moulding plate formed with projections or recesses corresponding to the openings 16 to obtain the nonwoven fabric which is then subjected to hot blast or heated under a pressure by use of heating rollers so as to fuse the individual fibers 15 together and thereby to fill up the fiber interstices to some degrees.

It is also possible to construct the topsheet 2 from only two zones, i.e., the zones of high water-resistance and low water-resistance. However, it should be understood that an abrupt change in the water-resistance from one zone to another zone may often lead to an abrupt change in the sheet strength and as a result the sheet may be apt to be torn along the region in which such abrupt change occurs. Accordingly, the topsheet should be preferably constructed so that the water-resistance may be gradually decreased.

According to the invention, the fiber interstices in the skin-contacting area of the topsheet comprising the nonwoven fabric are filled up to increase the water-resistance in this region and thereby to prevent the body fluids from flowing backward through the skin-contacting area, on one hand, and the fiber interstices are not filled up in the region substantially free from a possibility of body fluids' back flow so as to keep high air-permeability as well as soft touch peculiar to the nonwoven fabric, on the other hand. The nonwoven fabric is preferably made of thermoplastic synthetic fibers of a small fineness to obtain said soft touch.

What is claimed is:

1. A topsheet for use in a body fluids absorptive good including a crotch area, said topsheet consisting essentially of a nonwoven made of thermoplastic synthetic fibers appropriately fused together and defining a first zone of relatively high water-resistance and appreciable dimensional extent located at and extending over said crotch area and a second zone of relatively low water-resistance surrounding said first zone, the fabric including openings adapted to guide body fluids from a top surface of the topsheet to an absorbent core underlying a bottom surface of the topsheet.

2. A topsheet according to claim 1, wherein the fabric has a fiber region extending continuously around said openings.

3. A topsheet according to claim 1, wherein the water-resistance of said second zone gradually decreases as a distance from said first zone becomes longer.

4. A topsheet according to claim 1, wherein said first and second zones include fiber interstices more closely spaced than in a remaining zone.

5. The topsheet of claim 1, wherein said topsheet is formed with only two of said first zones.

6. A topsheet of claim 5, wherein said topsheet is formed with only one second zone extending substantially the entire longitudinal extent of the crotch area.

7. The topsheet of claim 6, wherein said two first zones are respectively located at opposite longitudinal ends of said one second zone.

8. The topsheet of claim 1, wherein said topsheet is formed with only one said first zone.

9. The topsheet of claim 8, wherein said one first zone extends longitudinally substantially the entire longitudinal extent of said crotch area.

10. The topsheet of claim 1, wherein said second zone is defined by an edge spaced inwardly from edges of the topsheet defining the crotch area and other edges of the topsheet defining longitudinally opposite front and rear edges of said topsheet.

11. A topsheet for use in a body fluids absorptive good including a crotch area, said topsheet comprising a nonwoven fabric made of thermoplastic synthetic fibers appropriately fused together and defining a first zone of relatively high water-resistance and appreciable dimensional extent located at and extending over said crotch area and a second zone of relatively low water-resistance surrounding said first zone, the fabric including openings adapted to guide body fluids from a top surface of the topsheet to an absorbent core underlying a bottom surface of the topsheet.

12. The topsheet of claim 11, wherein said topsheet is formed with only two of said first zones.

13. A topsheet of claim 12, wherein said topsheet is formed with only one second zone extending substantially the entire longitudinal extent of the crotch area.

14. The topsheet of claim 13, wherein said two first zones are respectively located at opposite longitudinal ends of said one second zone.

15. The topsheet of claim 11, wherein said topsheet is formed with only one said first zone.

16. The topsheet of claim 15, wherein said one first zone extends longitudinally substantially the entire longitudinal extent of said crotch area.

17. The topsheet of claim 11, wherein said second zone is defined by an edge spaced inwardly from edges of the topsheet defining the crotch area and other edges of the topsheet defining longitudinally opposite front and rear edges of said topsheet.

* * * * *